(12) United States Patent
Ullman et al.

(10) Patent No.: US 6,326,159 B1
(45) Date of Patent: Dec. 4, 2001

(54) RECEPTORS FOR IMMUNE COMPLEXES

(75) Inventors: Edwin F. Ullman, Atherton, CA (US); John Jelesko, Seattle, WA (US); Marcel R. Pirio, San Jose; Thomas D. Kempe, Sunnyvale, both of CA (US)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/300,572

(22) Filed: Sep. 2, 1994

Related U.S. Application Data

(63) Continuation of application No. 07/976,829, filed on Nov. 16, 1992, now abandoned, which is a continuation of application No. 06/916,777, filed on Oct. 9, 1986, now Pat. No. 5,223,441.

(51) Int. Cl.$^7$ .................. C07K 16/00; G01N 33/536; G01N 33/543; G01N 33/577
(52) U.S. Cl. .................. 435/7.7; 435/7.9; 435/7.94; 435/18; 435/21; 435/26; 435/28; 435/975; 436/507; 436/512; 436/518; 436/536; 436/537; 436/547; 436/548; 436/800; 436/804; 436/805; 436/808; 436/815; 436/817; 530/388.9; 530/389.8; 530/391.3; 530/808
(58) Field of Search .................. 435/7.7, 7.9, 7.94, 435/975, 18, 21, 26, 28; 436/507, 518, 537, 548, 815, 512, 536, 547, 800, 804, 805, 808, 817; 530/388.9, 389.8, 391.3, 808

(56) References Cited

U.S. PATENT DOCUMENTS

| | | | |
|---|---|---|---|
| 4,062,935 | 12/1977 | Mason et al. | 424/12 |
| 4,141,965 | 2/1979 | Soothill et al. | 424/12 |

(List continued on next page.)

FOREIGN PATENT DOCUMENTS

| | | |
|---|---|---|
| 0 027 567 A1 | 4/1981 | (EP) . |
| 0 174 652 A3 | 3/1986 | (EP) . |
| 2161165 | 1/1986 | (GB) . |

(List continued on next page.)

OTHER PUBLICATIONS

Bekisz, et al., *Chemical, Abstracts*, vol. 103: Abstract #176791t, p. 548 (1985).

Nemazee, et al., *Proc. Natl. Acad. Science, USA*, vol. 79: pp 3828–3832 (Jun. 1982).

Nemanzee, et al., Proc. Natl. Acad. Sci. USA, (Jun. 1982) vol. 79: pp 3828–3832, "Enhancing antibody: A novel component of the immune response".

Owens, et al., Clinical Chemistry, (Apr. 1981) vol. 27:4, pp. 619–624, "$^{125}$I radioimmunoassay of delta–9–tetrahydrocannabinol in blood and plasma with a solid–phase second antibody separation method".

*Primary Examiner*—David Saunders
(74) *Attorney, Agent, or Firm*—Theodore J Leitereg

(57) ABSTRACT

Receptors are disclosed that are antibodies that exhibit a binding affinity for an immune complex of a monoepitopic antigen and an antibody for such antigen that is substantially greater than the binding affinity for the monoepitopic antigen or the antibody for the monoepitopic antigen apart from the immune complex. Normally, the monoepitopic antigen has a molecular weight less than 1500 and is an organic compound. The antibodies of the present invention find use in a method for determining a monoepitopic antigen in a sample suspected of containing such antigen. The method comprises forming an immune sandwich complex comprising the monoepitopic antigen or an analog thereof, a first monoclonal antibody that binds to the monoepitopic antigen, and a second monoclonal antibody that is an antibody of the present invention and detecting the immune sandwich complex. Compositions of matter and kits for use in conducting an assay in accordance with the invention as well as methods for producing the above receptors are also disclosed.

121 Claims, 2 Drawing Sheets

U.S. PATENT DOCUMENTS

| | | | |
|---|---|---|---|
| 4,281,061 | 7/1981 | Zuk et al. | 436/513 |
| 4,420,461 | 12/1983 | Reckel et al. | 422/61 |
| 4,459,359 | 7/1984 | Neurath | 436/507 |
| 4,471,058 | 9/1984 | Smith et al. | 436/518 |
| 4,474,892 | 10/1984 | Murad et al. | 436/513 |
| 4,486,530 | 12/1984 | David et al. | 435/7 |
| 4,514,505 | 4/1985 | Canfield et al. | 436/500 |
| 4,536,479 | 8/1985 | Vander-Mallie | 436/537 |
| 4,544,640 | 10/1985 | Soma et al. | 436/548 Y |
| 4,670,383 | 6/1987 | Baier et al. | 435/28 X |
| 4,828,985 | 5/1989 | Self | 435/7 |
| 4,840,895 | 6/1989 | Self | 435/7 |

FOREIGN PATENT DOCUMENTS

| | | |
|---|---|---|
| 2 171 999 A | 9/1986 | (GB) . |
| 2177094 A | 1/1987 | (GB) . |
| WO 85/04422 | 10/1985 | (WO) . |
| WO 87/07147 | 12/1987 | (WO) . |
| WO 88/00240 | 1/1988 | (WO) . |

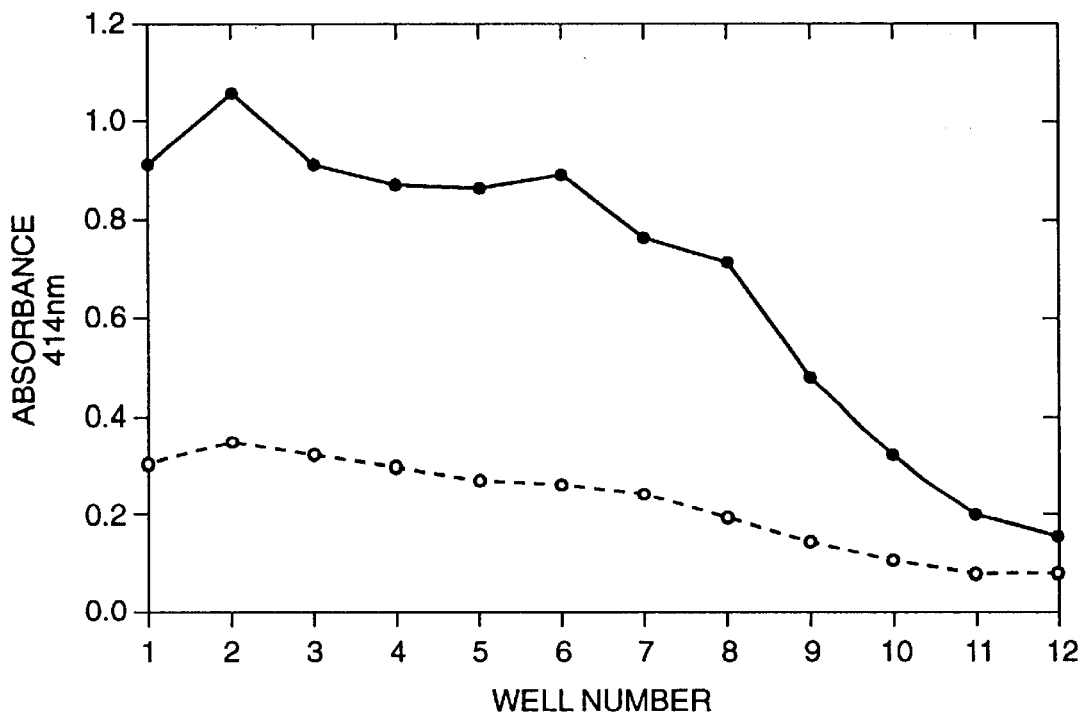
FIG._1
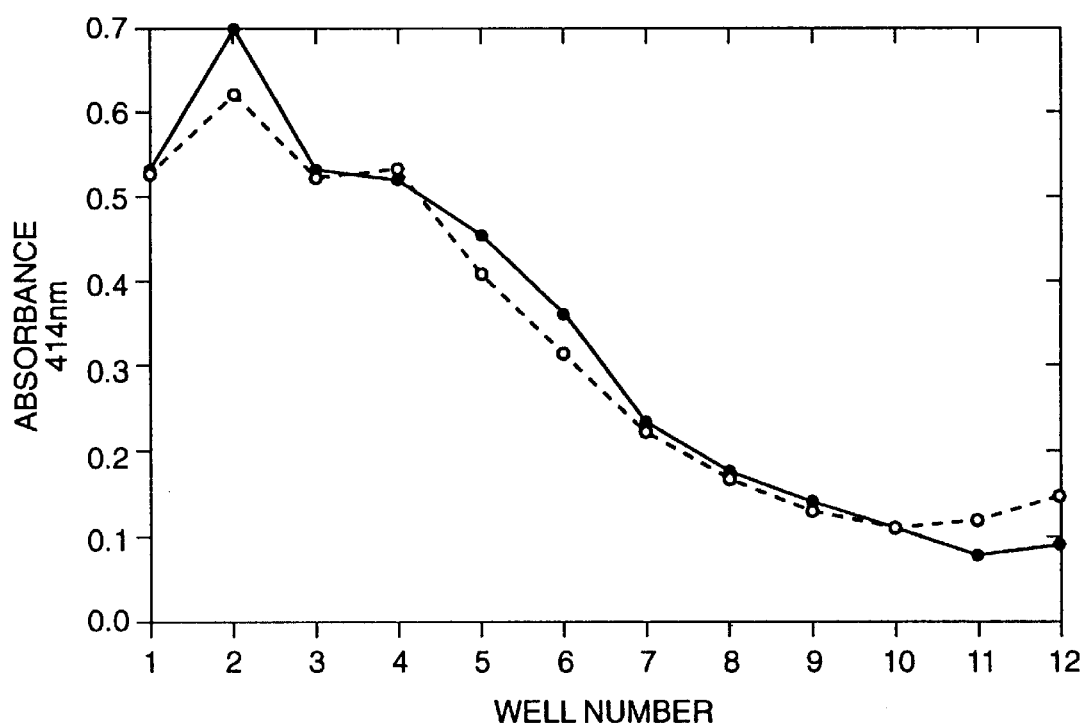
FIG._2

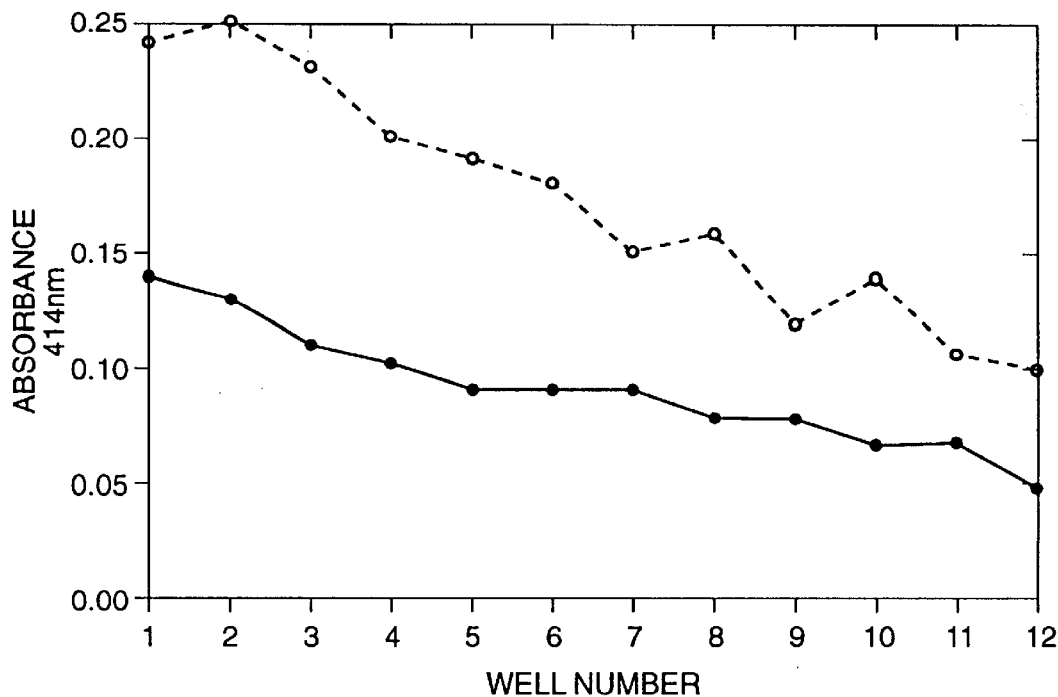
FIG._3
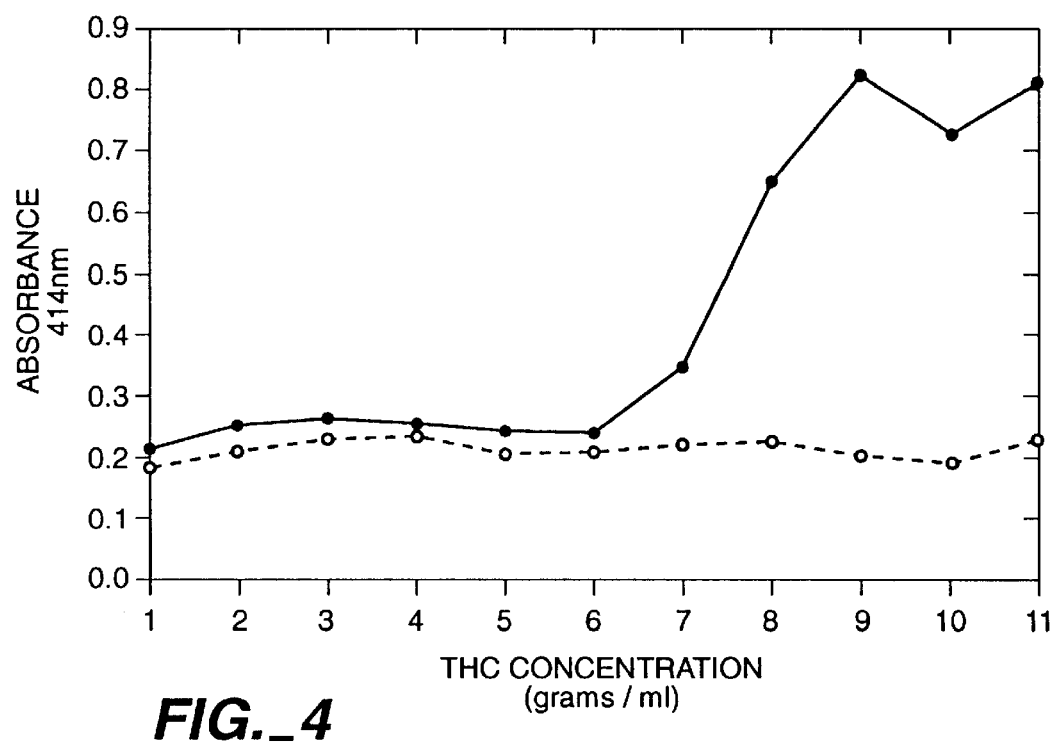
FIG._4

RECEPTORS FOR IMMUNE COMPLEXES

This is a file wrapper continuation of application Ser. No. 07/976,829, filed of Nov. 16, 1992 is now abondoned, which in turn is a continuation of Ser. No. 06/916,777, filed Oct. 9, 1986 U.S. Pat. No. 5,233,441 which issued on Jun. 29, 1993.

BACKGROUND OF THE INVENTION

1. Field of the Invention

There is a continuing and increasing need for accurate, sensitive techniques for measuring trace amounts of organic materials in a wide variety of samples. This need includes the measurement of drugs, naturally occurring physiological active compounds or nutrients in physiological fluids, the presence of trace amounts of contaminants or toxic materials in foods, water or other fluids, and the like, as well as monitoring materials for trace contamination introduced during chemical processing.

Among the various techniques which have found increasing exploitation are techniques involving receptors which recognize or bind to a specific polar and spatial organization of one or more molecules. For the most part, the receptors are antibodies and the techniques are referred to as immunoassays. These techniques conventionally employ a labelled ligand, where the binding to the receptor allows for distinguishing between a bound labelled ligand and an unbound labelled ligand. Certain techniques, generally referred to as heterogeneous, rely on segregating the bound from the unbound labelled ligand. Other techniques, generally referred as homogeneous, rely on the bound labelled ligand providing a signal level different from unbound labelled ligand.

Methods are known for the detection of polyvalent antigens wherein at least two different binding sites on the antigen are used. Two-site immunometric assays are well known. They are used to detect the presence or concentration of a multideterminant antigen in a liquid sample. They involve reacting the antigen with both an immobilized antibody directed against one of the antigenic determinants and an antibody that is directed against another of the antigenic determinants and is indirectly or directly labelled to permit detection of the resulting immune complex. It is also known to use polyclonal antibodies, monoclonal antibodies, or a combination of both polyclonal and monoclonal antibodies. The use of two antibodies in the immunoassay enhances the sensitivity of the assay by permitting the use of excess antibody to ensure complete binding of antibody to all of the analyte in the sample. The use of monoclonal antibodies in a two-site immunoassay in some cases also increases the specificity of the assay by requiring the presence of two epitopic sites on the same molecule to produce a positive result.

While such assays involving two antibodies are useful where the analyte is a polyvalent antigen, the benefits realized by employing two antibodies are not available for monoepitopic antigens such as drugs or other organic compounds.

2. Description of the Related Art

The use of double antibodies for enhanced sensitivity in immunoassays is described in U.S. Pat. No. 4,281,061. Two-site immunoassays using monoclonal antibodies of different classes or subclasses and test kits for performing such assays are disclosed in U.S. Pat. No. 4,474,892. A method for the detection and/or determination of a polyvalent antigen using at least two different monoclonal antibodies is described in U.S. Pat. No. 4,471,058. U.S. Pat. No. 4,486,530 discloses immunometric assays using monoclonal antibodies. Monoclonal antibody mixtures and their use for enhanced sensitivity in immunoassays is discussed in U.S. Pat. No. 4,514,505. The use of anti-idiotype antibodies in immunoassays is discussed in U.S. Pat. No. 4,536,479. U.S. Pat. No. 4,062,935 discloses an immunoassay involving the binding of RF to the antigen-antibody complex. Sensitive immunoassays of antigens or antibodies sequestered within immune complexes is disclosed in U.S. Pat. No. 4,459,359. An assay of immune complexes is discussed in U.S. Pat. No. 4,141,965. U.S. Pat. No. 4,420,461 discloses agglutination-inhibition test kits for detecting immune complexes. An enhancing antibody being a novel component of the immune response is described by Nemazee, et al., *Proc. Natl. Acad. Sci., USA*, 79:3828–3832 (1982).

SUMMARY OF THE INVENTION

Compositions and methods are provided for conducting an immunoassay. One aspect of the present invention includes antibodies exhibiting a binding affinity for an immune complex of a monoepitopic antigen and an antibody for such antigen that is substantially greater than the binding affinity for the monoepitopic antigen or the antibody for the antigen apart from the immune complex. Normally, the monoepitopic antigen has a molecular weight: of less than about 1500 and the antibody is a monoclonal antibody. The antibodies of the invention can be bound to a label for use in immunoassays.

Another aspect of the invention includes compositions comprising an immune sandwich complex of a monoepitopic antigen or analog thereof, a first antibody that binds to the monoepitopic antigen, and a second antibody that exhibits a binding affinity for an immune complex of the monoepitopic antigen or analog thereof and a first antibody that is substantially greater than the binding affinity for the monoepitopic antigen or the first antibody apart from the immune complex.

Another aspect of the invention includes methods for preparing an antibody that binds to an immune complex of a monoepitopic antigen and a first antibody. In the methods animals are immunized with the first antibody affinity labeled with its complementary antigen.

Another aspect of the present invention includes methods for determining a monoepitopic antigen in a sample suspected of containing the antigen. The method comprises forming an immune sandwich complex comprising the monbepitopic antigen or analog thereof, a first antibody that binds to the monoepitopic antigen, and a second antibody that exhibits a binding affinity for the immune complex of the monoepitopic antigen and the first antibody that is substantially greater than the binding affinity for the monoepitopic antigen or the first antibody apart from the immune complex. The immune sandwich complex is then detected, the presence of said complex being related to the amount of monoepitopic antigen in the sample.

Another aspect of the present invention concerns improvements in homogeneous assays for the determination of a monoepitopic antigen in a sample suspected of containing such antigen. Such homogeneous assays normally comprise the steps of (a) combining in an aqueous medium the sample, labelled monoepitopic antigen, and a first antibody that binds to the monoepitopfc antigen and (b) determining the effect of the sample on the amount of labelled monoepitopic antigen that binds to the first antibody. The improvement of the present invention comprises adding to the aqueous medium a second antibody that exhibits a binding affinity for the immune complex of the monoepitopic antigen and the first antibody that is substantially greater than the binding affinity for the monoepitopic antigen or the first antibody apart from the immune complex.

The invention further includes kits for use in conducting an assay for analyte in a sample suspected of containing the analyte. The kit comprises in packaged combination an antibody that exhibits a binding affinity for an immune complex of a monoepitopic antigen and an antibody for such antigen that is substantially greater than the binding affinity for the monoepitopic antigen or the antibody for the antigen apart from the immune complex.

BRIEF DESCRIPTION OF THE DRAWINGS

FIG. 1 is a graphic depiction of a THC ELISA according to Examples 8 and 9 herein employing a monoclonal antibody in accordance with the present invention. =present, =no THC FIG. 2 is a graphic depiction of a THC ELISA according to Examples 8 and 9 herein employing an anti-idiotype monoclonal antibody; this depiction is provided by way of comparison only and is not part of the present invention. =THC present, =no THC FIG. 3 is a graphic depiction of a THC ELISA according to Examples 8 and 9 herein employing a paratope-specific monoclonal antibody; this depiction is provided by way of comparison only and is not part of the present invention. =THC present, =no THC FIG. 4 is a graphic depiction of an ELISA according to Examples 8 and 9 herein employing a monoclonal antibody in accordance with the present invention under constant antibody and conjugate concentrations. =THC present, =no THC.

DESCRIPTION OF THE SPECIFIC EMBODIMENTS

The present antibodies, methods, compositions, and kits provide for improved immunoassays. The invention finds utility in sandwich type assays which heretofore were not available for monoepitopic antigens. Furthermore, the present invention provides for enhanced sensitivity and specificity in homogeneous assays.

Before proceeding further with a description of the specific embodiments of the present invention, a number of terms will be defined.

Analyte—an antigen, normally a monoepitopic antigen, to be measured that is capable of binding specifically to an antibody, that may be a drug, hormone, pesticide, environmental pollutant, toxin, and the like. The precise nature of monoepitopic antigens and drug analytes together with numerous examples thereof are disclosed in U.S. Pat. No. 4,299,916 to Litman, et al., particularly columns 16 to 23, and in U.S. Pat. No. 4,275.149, columns 17 and 18, and in U.S. Pat. No. 4,275,149, columns 17 and 18, the disclosures of which are incorporated herein by reference.

The analytes will generally be compounds having a, molecular weight less than about 1500, usually from about 100 to 1,500 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethoiphan, their derivatives and metabolites; cocaine alkaloids, which include cocaine and benzoyl ecgonine, their derivatives and metabolities, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, estogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the Vitamins such as A, B, e.g., $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

"Monoepitopic antigen"—an antigen that can bind strongly ($K>10^6 M^-$) to only one antibody or to any one of a multiplicity of strongly binding antigen specific antibodies wherein binding to any one such antibody substantially weakens or inhibits binding to any other such antibody.

"Antigen analog"—a modified monoepitopic antigen which can compete with the unmodified monoepitopic antigen for an antibody, the modification providing at least a means to join the antigen to another molecule. The antigen analog will usually differ from the antigen by more than replacement of a hydrogen with a bond and will usually be linked to a hub or label, but need not.

"Antibody"—an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal). Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like.

"Antibody for the antigen"—an antibody specific for a monoepitopic antigen or an antigen analog, sometimes referred to herein as the first antibody. The antibody will usually be monoclonal.

"Antibody for an immune complex"—an antibody that exhibits a single site affinity constant for binding to an immune complex of a monoepitopic antigen and an antibody for such monoepitopic antigen that is substantially, i.e., at least two-fold, preferably at least ten-fold, greater than the single site affinity constant for binding to the monoepitopic antigen or the antibody for such monoepitopic antigen apart from the immune complex, sometimes referred to herein as the second antibody.

Preferably, the second antibody is a monoclonal antibody. The monoclonal antibodies useful in the present invention can be obtained by the process discussed by Milstein and Kohler and reported in *Nature*, 256:495–497, 1975. The details of this process are well known and will not be repeated here. However, basically it involves injecting a host, usually a mouse or other suitable animal, with an immunogen. The mouse is subsequently sacrificed and cells taken from its spleen. Alternatively, the host may be unsensitized spleen cells, which are sensitized to the immunogen in vitro. The resulting cells are fused with myeloma cells. The result is a hybrid cell, referred to as a hybridoma," that can be cultured in vitro. The population of hybridomas is screened and manipulated so as to isolate individual clones each of which secretes a single antibody to the antigen.

The antibodies produced by the individual hybrid cell lines are screened in the present invention to identify those having high affinity for the immune complex of the antigen and antibody for the antigen and low binding affinity for the antigen or the antibody for the antigen apart from the immune complex. In the present invention the immunogenic substance employed is an immune complex between the monoepitopic antigen or antigen analog and its cognate antibody. Such immune complex involves binding between the antigen and its cognate antibody at the binding site. Means must be provided to avoid dissociation of the immune complex both before and during the immunization process. One approach to assure stability of the immune complex involves "affinity labeling," that is, conjugating the antibody binding site to a chemically activated antigen analog. Groups and methods for chemically activating antigens are well-known in the art as well as their use in affinity labeling. See, for example, J.P. Tite, et al., *Immunology* (1981) 42:355. However, the use of the affinity labeled material as an immunogen in accordance with the present invention is not known. The method can involve the use of a chemically active group attached to the antigen that will react with a group near the antibody binding site. Usually, the chemically active group should not react so rapidly with groups found on the protein that the non-covalent binding to the binding site cannot be substantially complete prior to substantial reaction. This can be achieved by selecting groups of appropriate reactivity or by selecting groups that have low reactivity under the neutral binding conditions and can be activated by subsequently changing the conditions, e.g., by changing pH or temperature. Activated acids are particularly useful including active esters (NHS, nitrophenyl), acid azides, mixed anhydrides, thioesters and the like. These groups react primarily with amines and can be attached to chains bound to the antigen, the length of which are selected to permit reaction with an amine adjacent to the binding site. Other groups include acylating agents such as haloacetamides, maleimides, acrylamides, haloketones, diazoketones, diazoesters, tosylates, triflates, etc.

Another method of affinity labeling utilizes photochemical activation. For some antigens that absorb light of wavelengths longer than 300 nm, irradiation of the immune complex can directly produce covalent bonding to the antibody. When this is not possible, a photosensitive group is attached to the antigen. Arylazides and diazoketones are frequently used.

After labeling, it is desirable to purify the product by immunoadsorption with solid phase bound antibody. Further purification can be achieved by adsorption with solid phase bound antigen.

Various techniques exist for enhancing yields of monoclonal antibodies and various conventional ways exist for Isolation and purification of the monoclonal antibodies, so as to free the monoclonal antibodies from other proteins and other contaminants (see, for example, Köhler and Milstein, supra).

Also included within the scope of the invention are useful binding fragments of the second antibody such as Fab, Fab', F(ab')$_2$, Fv, dnd so forth. Tho antibody fragments are obtained by conventional techniques. For example, useful binding fragments may be prepared by peptidase digestion of the antibody using papain or pepsin.

The second antibody can be from a murine source, mammalian source including human, or other sources, or combinations thereof. Included within the scope of this invention are antibodies of classes such as IgG, IgM, IgA, IgE, and the like, including isotypes within such classes.

"Immune complex"—a complex formed between an antigen or antigen analog and its cognate antibody as a result of the binding affinity of the antibody for the antigen or antigen analog.

"Label"—a label may be any molecule conjugated to an analyte or an antibody, or to another molecule. In the subject invention, the label can be a member of the signal producing system that includes a signal producing means. The label may be isotopic or nonisotopic, preferably nonisotopic. By way of example and not limitation, the label can be a catalyst such as an enzyme, a co-enzyme, a chromogen such as a fluorescer, dye or chemiluminescer, a radioactive substance, a dispersible particle that can be non-magnetic or magnetic, a solid support, a liposome and so forth.

"Signal producing means"—means capable of interacting with the label to produce a detectible signal. Such means include, for example, electromagnetic radiation, heat, chemical reagents, and the like. Where chemical reagents are employed, some of the chemical reagents can be included as part of a developer solution. The chemical reagents can include substrates, coenzymes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to other molecules or to a support.

"Signal Producing System"—The signal producing system may have one or more components, at least one component being the label. The signal producing system includes all of the reagents required to produce a measurable signal including signal producing means capable of interacting with the label to produce a signal.

The signal producing system provides a signal detectable by external means, normally by measurement of electromagnetic radiation, desirably by visual examination. For the most part, the signal producing system includes a chromophoric substrate and enzyme, where chromophoric substrates are enzymatically converted to dyes which absorb light in the ultraviolet or visible region, phosphors or fluorescers.

The signal-producing system can include at least one catalyst as a label, usually at least one enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of bound and unbound label. Where enzymes are employed, the involved reactions will be, for the most part, hydrolysis or redox reactions.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. A wide variety of non-enzymatic catalysts which may be employed are found in U.S. Pat. No. 4,160,645, issued Jul. 10, 1979, the appropriate portions of which are incorporated herein by reference.

An enzyme or coenzyme is employed which provides the! desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in U.S. Pat. No. 4,275,149 bridging columns 19 to 23, and U.S. Pat. No. 4,318,980, columns 10 to 14, which disclosures are incorporated herein by reference.

A number of enzyme combinations are set forth in U.S. Pat. no. 4,275,149, bridging columns 23 to 28, which combinations can find use in the subject invention. This disclosure is incorporated herein by reference.

"Poly(ligand analog)"—a plurality of ligand analogs joined together covalently, normally to a hub nucleus. The hub nucleus is a polyfunctional material, normally polymeric, usually having a plurality of functional groups, e.g., hydroxyl, amino, mercapto, ethylenic, etc., as sites for linking. The hub nucleus may be water soluble or insoluble, preferably water soluble, and will normally be at least about 30,006 molecular weight and may be 10 million or more molecular weight. Illustrative hub nuclei include polysaccharides, polypeptides (including proteins), nucleic acids, anion exchange resins, and the like. Water insoluble hub nuclei can also include walls of containers, e.g., glass or plastic, glass beads, addition and condensation polymers, Sephadex and Agarose beads and the like.

"Support"—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly (vinyl butyrate), etc.; either used by themselves or in conjunction with other materials; glass, ceramics, metals, and the like.

Ancillary Materials—Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or. surfactants, particularly non-ionic surfactants, binding enhancers, e.g., polyalkylene glycols, or the like.

As mentioned above, one aspect of the present invention concerns an antibody that exhibits a binding affinity for an immune complex of a monoepitopic antigen and an antibody for such antigen that is substantially greater than the binding affinity for the monoepitopic antigen or the antibody for such antigen apart from the immune complex. Preferably such antibody is a monoclonal antibody.

One such monoclonal antibody in accordance with the present invention, by way of example and not limitation, is a novel antibody designated THC AIC 10-4. This monoclonal antibody exhibits a binding affinity for an immune complex of tetrahydrocannabinol (THC) and a monoclonal antibody for THC that is substantially greater than the binding affinity for THC or the antibody for THC apart from the immune complex. The binding affinity for the monoclonal antibody of the invention for the immune complex is approximately five times greater than the binding affinity for the THC or the antibodies for the THC alone. This monoclonal antibody in accordance with the invention is of the IgGl isotype. The antibody THC AIC 10-4 is produced by a murine hybridoma.

The novel antibodies of the present invention can provide enhanced specificity. The antibodies recognize the immune complex of the monoepitopic antigen and an antibody specific for such antigen. As a result of the independent binding of the two antibodies, less interference from other molecules can occur. The antibodies of the invention find particular use in immunoassays, but may also be used in other applications requiring high specificity or high affinity antibodies such as in affinity purifications, and have potential use in vivo for eliciting a cell mediated response from a monoepitopic drug.

In immunoassays the present invention has particular Iapplication to the determination of monoepitopic antigen analytes, for example, drugs. As mentioned above the present assay method has application both to heterogeneous and homogeneous assays. Exemplary of heterogeneous assays are the radioimmunoassay (RIA, Yalow and Berson, J. Clin. Invest. (1960) 39, 1157), and enzyme linked immunoassays such as the enzyme linked immunosorbant assay (ELISA), see "Enzyme-Immunoassay" by Edward T. Maggio, CRC Press Incorporated, Boca Raton, Fla., 1980.

Homogeneous immunoassays are exemplified by enzyme multiplied immunoassay techniques (e.g. see U.S. Pat. No. 3,817,837), immunofluorescence methods such as those disclosed in U.S. Pat. No. 3,993,345, enzyme channeling techniques such as those disclosed in U.S. Pat. No. 4,233,402, and other enzyme immunoassays as discussed in Maggio, supra.

The assay for the analyte will normally be carried out in an aqueous buffered medium at a moderate pH, generally that which provides optimum assay sensitivity. The assay can be performed either without separation (homogeneous) or with separation (heterogeneous) of any of the assay components or products.

The aqueous medium may be solely water or may include from 0 to 40 volume percent of a cosolvent. The pH for the medium will usually be in the range of about 4 to 11, more usually in the range of about 5 to 10, and preferably in the range of about 6.5 to 9.5. The pH will usually be a compromise between optimum binding of the binding members and the pH optimum for other reagents of the assay such as members of the signal producing system.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred.

Moderate temperatures are normally employed for carrying out the assay and usually constant temperatures during the period of the measurement, particularly for rate determinations. Incubation temperatures will normally range from about 5° to 45° C., more usually from about 15° to 40° C. Temperatures during measurements will generally range from about 10° to 50°, more usually from about 15° to 40° C.

The concentration of analyte which may be assayed will generally vary from about $10^{-4}$ to $10^{-15}$ M, more usually from about $10^{-6}$ to $10^{-14}$ M. Considerations, such as whether the assay is qualitative, semiquantitative or quantitative, the particular detection technique and the concentration of the analyte of interest will normally determine the concentrations of the various reagents.

While the concentrations of the various reagents in the assay medium will generally be determined by the concentration range of interest of the analyte, the final concentration of each of the reagents will normally be determined empirically to optimize the sensitivity of the assay over the range. That is, a variation in concentration of the analyte which is of significance should provide an accurately measurable signal difference.

While the order of addition may be varied widely, there will be certain preferences depending on the nature of the assay. The simplest order of addition is to add all the materials simultaneously and determine the affect that the assay medium has on the signal producing system as in a homogeneous assay. Alternatively, the reagents can be combined sequentially. Optionally, an incubation step may be involved subsequent to each addition, generally ranging from about 30 seconds to 6 hours, more usually from about 2 minutes to 1 hour.

In a homogeneous assay after all of the reagents have been combined either simultaneously or sequentially, the affect of the assay medium on the signal producing system is determined. The effect of the assay medium on the signal producing system is related to the amount of the monoepitopic analyte in the sample tested. The novel antibody of the invention is added preferably after addition of the sample containing the antigen analyte and the antibody for the analyte. The amount of antibody of the invention employed in a homogeneous assay depends on the nature of the monoepitopic antigen and of the antigen-label conjugate. Such amounts of reagents are set out in U.S. Pat. No. 3,817,837, particularly at column 4, the relevant disclosure of which is incorporated herein by reference. The use of the antibodies of the invention in homogeneous assays increases the sensitivity and/or specificity of the assays by enhancing the effective binding between the monoepitopic antigen and antibody for such antigen. The antibody of the invention combines with the immune complex of the monoepitopic antigen analyte and antibody for the analyte decreasing the dissociation of this immune complex during the homogeneous assay. An example of a homogeneous assay is the enzyme multiplied immunoassay technique described in U.S. Pat. No. 3,817,837, the disclosure of which is incorporated herein by reference in its entirety.

A particular embodiment of the present invention involves the detection of monoepitopic antigens by means of a sandwich immunoassay. In the method an immune sandwich complex is formed comprising the monoepitopic antigen or an analog thereof, a first monoclonal antibody that binds to the antigen and a second monoclonal antibody that exhibits a binding affinity for the immune complex of the antigen and its cognate antibody that is substantially greater than the binding affinity for the antigen or its cognate antibody apart from the immune complex. Subsequently, the immune sandwich complex is detected and is related to the amount of the monoepitopic antigen analyte in the sample. The immune sandwich complex is detected by virtue of the presence in the complex of a label wherein either or both the first antibody and the second antibody contain labels or substituents capable of combining with labels such as linking the antibody to biotin and providing avidin bound to a label.

The immune sandwich complex assay involving the novel antibody of the present invention may be conducted in a heterogeneous mode or it may be conducted in a homogeneous mode. The novel approach of the present invention allows one to use an excess of one or both antibodies for the monoepitopic antigen in order to increase the rate of reaction.

The immune sandwich complex assays for polyvalent antigens are well known and, for the most part, protocols for such assays may be utilized for monoepitopic antigens employing the novel antibodies of the present invention. Such sandwich type assays are disclosed in, for example, U.S. Pat. No. 4,486,530, the disclosure of which is incorporated herein by reference in its entirety. The immune sandwich complex assay may be conducted by having the second antibody bound to a support. The immune sandwich complex thus becomes bound to a support if the monoepitopic antigen analyte is present in the sample. The sample suspected of containing the analyte can be combined with the first antibody and the combination subsequently combined with the second antibody. On the other hand the reagents can be combined simultaneously.

Another example of a method in which the immune sandwich complex assay utilizing the novel antibodies of the present invention can be employed is the concentrating zone method in heterogeneous immunoassay disclosed in U.S. Pat. No. 4,366,241, the disclosure of which is incorporated herein by reference in its entirety. In the concentrating zone method a device is employed having a small test zone wherein a binding pair member is bound. In accordance with the present invention the binding member in the test zone can be the novel monoclonal antibody of the invention. The test zone is in liquid communication with a large liquid absorbing zone, which serves to draw liquid through the test zone, store liquid and may serve to control the rate at which the liquid is drawn through the test zone. The sample suspected of containing the monoepitopic antigen analyte is combined in an aqueous medium with an antibody for such antigen. The aqueous medium is then contacted with the test zone. In this particular approach the antibody for the monoepitopic antigen can be bound to a label as part of a signal producing system. Alternatively, one could bind the antibody for the monoepitopic antigen in the test zone. The test zone would be contacted with the aqueous medium containing the sample to be analyzed and with the novel antibody of the present invention. If analyte is present in the sample the novel antibody of the invention would bind in the test zone. The antibody of the invention would carry a label as part of a signal producing system.

Another immunoassay in which the present invention can be applied is described in U.S. Pat. No. 4,533,629, the disclosure of which is incorporated herein by reference in its entirety. This method involves the simultaneous calibration heterogeneous immunoassay. Two surfaces are provided generally in juxtaposition. One surface is a measurement surface and the other surface is a calibration surface. Applying the present invention to the simultaneous calibration assay the measurement surface can contain antibody for the monoepitopic antigen analyte. An assay medium containing the sample to be analyzed is contacted with the measurement surface. Subsequently, the measurement surface is contacted with an aqueous medium containing the novel antibody of the present invention bound to a label. If analyte is present in the sample, the novel antibody of the invention would bind at the measurement surface and the label in conjunction with the other members of the signal producing system would produce a signal. Alternatively, the novel antibody of the invention can be bound at the measurement surface. An aqueous medium containing the sample and an antibody for the monoepitopic antigen analyte is contacted with the surface. The antibody for the analyte contains a label and the presence of a signal at the measurement surface would be indicative of the presence of the analyte in the sample.

Another example of assay in which the present invention may be employed is described in U.S. patent application Ser. No. 701,464, filed Feb. 14, 1985, for a Concentrating Immunochemical Test Strip. The disclosure of this application is incorporated herein by reference in its entirety. The method and device are for determining the presence of an analyte in a sample suspected of containing the analyte. The method involves contacting a test solution containing the sample and the first member of a specific binding pair with an end portion of a test strip of bibulous material capable of being transversed by the test solution through capillary action. The first member of the specific binding pair is capable of binding the analyte. The strip contains a second member of a specific binding pair integral therewith for concentrating and non-diffusively binding the first specific binding pair member at a small situs on the strip separated from the end portion of the strip. A detectible signal is produced in relation to the presence of the analyte in the test solution. Applying the present invention to the method and device, the small situs can contain a novel monoclonal antibody of the present invention. The sample suspected of containing the monoepitopic antigen analyte and antibody for such analyte are combined in an aqueous medium. The medium is contacted with an end portion of the strip and allowed to migrate along the strip by capillary action. If analyte is present in the sample, an immune complex will form between the analyte and its cognate antigen. This immune complex will then be captured at the situs. Members of a signal producing system are employed to generate a signal at the situs as a result of the captured immune complex. On the other hand, if analyte is not present in the sample no immune complex will form and be captured when the aqueous medium containing the sample and the antibody for the analyte is contacted with the end portion of the strip and allowed to migrate along the strip by capillary action to the situs. Therefore, no signal will be produced at the situs thereby indicating the absence of analyte in the sample.

Another aspect of the present invention involves a composition comprising an immune sandwich complex of a monoepitopic antigen, a first antibody that binds to said antigen, and a second antibody that exhibits a binding affinity for an immune complex of said antigen and said first antibody that is substantially greater than the binding affinity for said antigen or said first antibody part from said immune complex.

To enhance the versatility of the subject invention, he reagents can be provided in packaged combination, in the same or separate containers, so that the ratio of the reagents provides for substantial optimization of the method and assay. The kit comprises as one reagent an antibody that exhibits a binding affinity for an immune complex of a monoepitopic antigen and an antibody for such antigen that is substantially greater than the binding affinity for the antigen or the antibody apart from the immune complex. The kit further includes other separately packaged reagents for conducting an assay including members of the signal producing system, other antibodies, and so forth.

EXAMPLES

The invention is demonstrated further by the following illustrative examples.

Before proceeding with a description of the Examples, the following terms are defined:

| | |
|---|---|
| PBS | 0.01M NaH$_2$PO$_4$, 0.15M NaCl, 0.02% NaN$_3$ |
| IgG | immunoglobulin G |
| IgA | immunoglobulin A |
| IgM | immunoglobulin M |
| EIA | enzyme immunoassay |
| MAb | monoclonal antibody |
| Ab$_2$ | monoclonal antibody THC AIC 10-4 |
| IgG$_1$ | IgG$_1$ isotype of IgG |
| Ab$_1$ | monclonal antibody THC 2-57 |
| HRP | horse radish peroxidase |
| THC | tetrahydrocannibinal |
| ABTS | 2,2'-azinobis(3-ethylbenzthiazoline-sulfonic acid)-ABTS is a trademark |
| OD | optical density |
| DMEM | Dulbecco's modified Eagle's medium |
| ECDI | 1-ethyl-3-(3-dimethylaminopropyl) carbodiimide hydrochloride |
| Ag8.653 | nonsecretor myeloma cell line from the A.T.C.C. |
| S-DMEM | supplemented DMEM |
| ENDLO | "Low in endotoxins", a trade name for bovine serum |
| NCTC | a defined cell culture medium from Gibco |
| HEPES | N-2-hydroxyethylpiperazine-N'-2-ethanesulfonic acid |
| CFA | complete freund's adjuvant |
| IFA | incomplete freund's adjuvant |
| MeOH | methanol |
| EtOAc | ethyl acetate |

-continued

| | |
|---|---|
| HOAc(AcOH) | acetic acid |
| tlc | thin layer chromatography |
| AIC | anti-immune complex, in accordance with the present invention. |

EXAMPLE 1

Synthesis of 11-nor-$\Delta^8$-THC-9-carboxylic acid, β-alanyl [1-$^{14}$C] (I)

42 mg (0.122 mmol) of 11-nor-$\Delta^8$-THC-9-carboxylic acid (Research Triangle Institute), 15.4 mg (0.134 mmol) of N-hydroxysuccimide and 27.6 mg (0.134 mmol) of N,N'-dicyclohexylcarbodiimide were combined with 3 ml of anhydrous tetrahydrofuran and stirred for 16 hours at ambient temperature. The reaction was monitored by tlc analysis, analtech silica gel GF 0.5:9.5 MeOH-$CH_2Cl_2$, visualized with 0.5% ceric sulfate in 5% $H_2SO_4$, heating, Rf ~0.67.

The above activated ester solution was added dropwise to a stirring solution of 3 ml 5% $NaHCO_3$ containing 32.8 mg (0.368 mmol) of β-alanine and 0.16 mg (0.0017 mmol) β-alanine [1-$^{14}$C], specific activity 54.4 mG/mmol. After 16 hours stirring, the solution was acidified with concentrated HCl to pH 3–4 and the organic solvent removed under a stream of nitrogen. The solution was extracted twice with 5 ml ethylacetate, dried with $MgSO_{41}$ concentrated and purified on 1–20×20 cm 1000 micron analtech silica gel GF plate, 0.5:9.5:0.05 MeOH-EtOAc-AcOH. The appropriate band was isolated and extracted, concentrated, and dried in vacuo yielding 22 mg, specific activity 0.287 mCi/mmol.

EXAMPLE 2

Synthesis of 11-nor-$\Delta^8$-THC-9-carboxylic acid, β-alanyl [1-$^{14}$]-β-alanyl (II).

47 mg (0.113 mmols) of 11-nor-$\Delta^8$-THC-9-carboxylic acid, β-alanyl [1-$^{14}$C], 13.4 mg (0.113 mmols) N-hydroxysuccinimide and 23.3 mg (0.113 mmol) N,N'-dicyclohexylcarbodiimide were combined with 10 ml anhydrous tetrahydrofuran and stirred at ambient temperature for 16 hours. The above solution was added to a vigorously stirring solution of 15.1 ng (0.169 mmol) β-alanine in 10 ml 5% $NaHCO_3$. After 15 hours stirring at ambient temperature, the product isolation was the same as for the compound of Example 1 yielding 35 mg; tlc analysis Analtech silica gel GF 0.5:9.5:0.05, MeOH-EtOAc-HOAc, Rf ~0.37 with specific activity 0.248 mCi/mmol.

EXAMPLE 3

Preparation of Monoclonal Antibody THC 2–57 (Ab)

Mice were immunized with a 11 carboxymethyl oxime derivative of $\Delta^9$ THC from Research Triangle Institute according to known procedures conjugated to keyhole limpet hemocyanin (KLH), according to standard procedures. A booster injection in saline was given intravenously 96 hours prior to fusion.

A. Hybridization Procedure:

Splenocytes were prepared by gentle perfusion of spleen with serum-free RPMI. Remaining tissue was broken with a tissue homogenizer. Single cell suspension was obtained by passing homogenate through sterile Nitex monofilament screen (Tobler, Ernst and Traber #HD-3-85). Splenocytes and Ag 8.653 cells were washed twice and mixed in 2:1 ratio. Cells were fused with polyethylene glycol (PEG-1450, Bethesda Research Labs) according to the procedure described in *Clin. Immunol Immunopathol.*, 23 172–178 (1982).

B. Tissue Culture:

All hybridomas and the nonsecretor myeloma cell lines Ag 8.653 were maintained in log phase of growth in S-DMEM with 15% fetal calf serum (FCS), 10% NCTC-109, 0.45 mM pyruvate, 1.0 mM oxaloacetic acid, 10 μg/ml bovine insulin, 2.0 mM L-glutamine and 50 μg/ml gentamicin.

C. Cloning:

Cloning of hybridoms was done in the presence of non-immune peritoneal macrophages. Peritoneal lavage from one mouse was distributed in 150 mL SDMEM. Hybridoma cells from 96 well plate were taken in 5 mL medium. They were then distributed in 100 μL aliquots in first column of 8 wells on 96 well plates. These cells were then serially diluted across the whole plate.

D. Screening for THC-Positive MAb's

Costar EIA microplates were coated with 10 μl/well of rabbit antimouse IgG+IgA+IgM(H+L) (Zymed Labs) at 5 μl/ml in PBS, pH 7.2 overnight at 4° C. Plates were blocked with 200 μl of the gammaglobulin fraction of non-immune sheep serum at 200 μl/ml. Hybridoma supernatants were added to each well and incubated, for 90 minutes. After washing the plates, a $\Delta^9$-THC-HRP conjugate was added to each well and incubated for 45 minutes. Plates were again washed and then developed with ABTS substrate and read at 415 nm on an automated plate reader. Wells with the highest OD's that also showed the greatest loss of color development in a replicate plate ELISA that contained 20 ng $\Delta^9$THC/ml in the conjugate step. Hybridoma THC 2–57 was chosen from a large group of monoclones produced and selected by this method.

E. Purification of THC 2–57 Antibody Monoclonal antibody THC 2–57 was purified with BioRad's Affi-Gel Protein A system (MAPS™) according to BioRad Bulletin 1172.

EXAMPLE 4

Growth of THC 2–57 By Hollow Fiber Culture

Materials/Methods.

THC 2–57 was grown up in SDMEM:
1) DMEM (Gibco labs #430–2100; 10 L packages)
2) 15% ENDLO Fetal Bovine calf serum (KC Biologics #3000)
3) 10% NCTC 109 (or NCTC 135) (Gibco #440–110)
4) 4 mM L-glutamine (Sigma G-5763)
5) 0.05 mg/mL gentamicin (Gibco #600–5750)
6) 1 mM sodium pyruvate (Gibco #320–1360)
7) 1 mM oxalacetic acid (Sigma 0–4126)
8) 0.01 mg (25 Iu/mg)/mL bovine insulin (Sigma I-5500)
9) 4.765 mg/mL HEPES buffer (Sigma H-3375)

Healthy log phase cells, at a density of approximately $5 \times 10^6$ viable cells/mL (as determined by Trypan Blue exclusion hemocytometry), were harvested for inoculation into a Vitafiber II hollow fiber growth cartridge (Amicon).

The hollow fiber cartridge was set up essentially as suggested by Amicon:

A magnetically stirred one liter medium vessel was connected by silicon tubing to a variable speed paristatic pump recirculating media at 100 mLs per minute thru the hollow fiber lumen (1000 $cm^2$ surface area).

$10^8$ cells suspended in 25 mLs of Super DMEM were inoculated into the extracapillary growth chamber. The hollow fiber cartridge and medium reservoir were then placed in a 370 convection incubator.

Three times weekly, 1 of media was replaced and 30 mLs of extracapillary supernatant (containing the concentrated antibody) was harvested. The supernatant was monitored for antibody production by agarose electrophoresis and then stored frozen (−20° C.).

EXAMPLE 5

Ab$_1$-HRP Conjugation

Twenty-five mg of HRP (horseradish peroxidase, Sigma grade VI) was incubated in 0.5 ml of 0.1 M Na-phosphate, pH 6.8, with 1.25% glutaraldehyde at room temperature overnight. This was equilibrated in Hanks saline using a G-25 column taking the first 2.0 ml eluted. Also, 10 mg of Protein A purified Abi (THC 2–57) was equilibrated, in Hanks saline solution using a G-25 column.

The next day the 2.0 ml of Ab$_1$ prep and the 2.0 ml glutaraldehyde-activated HRP prep were mixed together and kept at 4° C. for 24 hours. Then, 0.2 ml of 0.2 M glycine was added to the conjugate mixture and incubated for two hours at room temperature to react any residual glutaraldehyde, thereby blocking any further cross-linking.

After the blocking reaction was completed, the conjugate was dialyzed against PBS buffer overnight and purified using a 2×180 cm Bio-Gel A1.5 m gel filtration column to separate the unbound HRP. The first major peak eluted was pooled and used as the Ab$_1$-HRP conjugate stock solution.

EXAMPLE 6

Affinity labeling of Ab$_1$ IgG with 11-nor-Δ$^8$-THC-9-carboxylic acid, bis β-alanyl [1-$^{14}$C] β-alanyl (II)

3.0 mg (0.0062 mmols) of compound prepared as in Example 2 (previously dried over P$_2$O$_5$ at 100° C. under vacuo 0.5 mm for 8 hours) 1.0 mg (0.0087 mmols) N-hydroxysuccinimide, 1.5 mg (0.0073 mmols) N,N'-dicyclohexylcarbodiimide and 1 ml of anhydrous tetrahydrofuran were combined and stirred at ambient temperature for 16 hours. Tlc on analysis Merck silanized RP-2 silica gel plate 2:8, EtOAc-hexane indicates NHS ester formation was complete.

150 μl (0.45 mg) (9.2×10$^{-4}$)mmols ~) of the above solution was added dropwise to a stirring solution of 3.0 ml 49.6 mg (3.1~10$^{-4}$mmols) (THC 2–57) IgG, in phosphate buffer pH 8.5 and 0.5 ml dimethylformamide at 5–10° C. The solution was stirred for 16 hours at 4° C. and then subjected to gel filtration using a 10-fold volume of M-Sephadex G-50 column in PBS (10 mM Na$_2$HPO$_4$—NaH$_2$PO$_4$, 154 mM NaCl, pH 7.4).

Determination of the ratio $^{14}$C labeled THC to 2–57) IgG$_1$ after purification by gel filtration and affinity gels.

The $^{14}$C THC concentrations were determined by measuring cpm in 100 μl of protein solution diluted with 10 ml scintillation fluid and counted with Beckman LS 2800.

The protein concentrations were measured by use of extinction coefficient ~1.4×10$^5$ IgG at 280 nm or using the Lowry method.

The labeled IgG1 was subjected to 1.5 mL of each of Sepharose 4B-IgG$_1$ (2–57) (16 hr) and AH-Sepharose 4B-THC (15 min) affinity gels.

| Gel | [$^{14}$C-THC]/IgG$_1$] |
|---|---|
| m-Sephadex G-50 | 3.1 |
| Sepharose 4B IgG$_1$ | 2.4 |
| Sepharose 4B THC | 2.3 |
| Sepharose 4B IgG$_1$ | 2.1 |

The above sample was subjected to a method for determination of binding site nonavailability of covalently modified monoclonal antibody (THC 2–57)IgG$_1$ using the observation that G6PDH-THC conjugate when combined with unmodified (THC-2–57)IgG$_1$ forms a distinct immune complex band on the electrophoretic gel. This band appears approximately midpoint between the G6PDH-THC and (THC-2–57)IgG$_1$ bands. The above labeled (THC-2–57) IgG$_1$-$^{14}$C THC did not form an immune complex with excess of G6PDH-THC. Therefore, it was concluded that the sites are covalently occupied by the radiolabeled THC derivative.

EXAMPLE 7

Preparation of Affinity Gels Used to Purify Affinity Labeled (THC 2–57) IgG$_1$-THC Conjugate 1. Preparation of Cyanogen Bromide-activated Sepharose 4B coupled to (THC 2–57) IgG$_1$.

1 g of CNBr activated Sepharose 4B was washed and swollen in a medium fritted disc funnel for 15 minutes with 1 mM HCl, then washed with 200 mL 1 mM CHl. 15 mL of IgG$_1$ (THC 2–57) (10 mM PO$_4$, 145 mM NaCl, 0.05% NaN$_3$, pH 7.4) was placed in membrane tubing and dialyzed against 3×250 mL Coupling Buffer 0.2 M NaHCO$_3$—Na$_2$CO$_3$ pH 8.5 containing 0.5 M NaCl, for 4 hours each time. 1 g ~3.5 mL of the swollen and washed CNBr activated Sepharose 4B was washed with Coupling Buffer. The CNBr Sepharose 4B and 15 mL IgG$_1$ were combined with 20 ml of Coupling Buffer in a plastic serum container and mixed by end over end rotation for 2 hours at room temperature and then overnight to block remaining activated groups. The gel was washed into a M-sinstered filter funnel and washed alternating with acetate buffer (0.1 M, pH 4) and Coupling Buffer (0.2 M, pH 8.5). The gel was stored in 10 mM PO$_4$, 145 mM NaCl, 0.05% NaN$_3$, pH 7.4 at 4° C. (~7.5 mg IgG$_1$/mL gel).

2. Preparation of 11-nor-Δ$^8$-THC-9-carboxylic Acid Linked to AH-Sepharose 4B.

2 g AH-Sepharose 4B (10 μmols of NH$_2$ groups/mL) was swollen in M-fritted disc funnel and washed with 400 ml 0.5 M NaCl. 55 mg 160 μmols 11-nor-Δ$^8$-THC-9-carboxylic acid was dissolved in 10 mL of 1:1, H$_2$O pH 4.5:dioxane. The 10 mL ligand solution was added to 8 ml of gel and volume brought to iquid: gel ratio of 2:1. Then, 1.5 g ECDI added and mixed end over end 16 hours at room temperature. The gel was washed with 50% 4×50 mL each 1:1 H$_2$O-dioxane, 1:1 0.2 M NaHCO$_3$—Na$_2$CO$_3$-dioxane and then 1:1 acetate buffer (0.1 M, pH 4-dioxane). The gel was then washed with distilled water and stored in 10 mM PO$_4$, 145 mM NaCl, 0.05% NaN$_3$, pH 7.4 at 4° C.

EXAMPLE 8

Preparation of Ab$_2$

The standard techniques of Köhler and Milstein, supra were followed. Myeloma cells (P3-NS11l) were fused with spleen cells from an immunized Balb/c mouse. The immunogen used was Protein A purified THC 2–57 antibody ($Ab_1$), grown in hollow fiber culture, covalently linked to delta-8-THC via a bis-beta-alanine linker (see Examples 1–6). Female Balb/c mice were immunized interperitoneally (IP) three times with 250 μg/boost (1X CFA, 2X IFA) once every ten days. After resting for four months, the mice were hyperimmunized IP three times with 200 μg immunogen/boost once a day three days prior to fusion.

Cell fusions were carried out via polyethylene glycol treatment according to standard hybridoma procedures. Eventually, one well, 2G3, was selected which had good color development on the ELISA plate with THC and less color development on the replicate plate without THC (See method below in Example 9). This cell line from this well was renamed THC AIC 10-4 and was cloned on a 96 well tissue culture plate for further analysis.

ELISA results of the first cloning plate of THC AIC 10-4 showed a clonally specific reproducible immune complex activity. Cells were dispensed into wells across the top row, and then serially diluted down the plate. Culture supernatents were assayed for AIC activity as described. Results were not corrected for background, which was 0.15 for wells with no growth. The average absorbance in the presence of THC for wells with cell growth was 0.95, compared to 0.25 in the absence of THC.

Overgrown, and uncloned, culture supernatant from THC AIC 10-4 along with one idiotype specific antisera and one paratope specific antisera (the last two were diluted ascites samples) raised against THC 2-57 were retested in a titration experiment by mixing the antibodies with excess THC and then serially diluting the mixture across a plate in the immune complex ELISA protocol. The results from this experiment are shown in FIGS. 1–3.

The titration of the AIC antibody in FIG. 1 shows consistently higher readings in the presence of THC drug, dependant upon the $Ab_2$ concentration. The two control antibodies show responses for a typical anti-idiotype MAb (FIG. 3—no effect by the antigen for $Ab_1$) and a paratope-specific MAb (FIG. 2—competition with drug for binding to the antigenic site on $Ab_1$).

Similarly, overgrown culture supernatant from THC AIC 10-4 was also subjected to the immune complex ELISA under constant antibody and conjugate concentrations to show the dependence of the AIC response on THC. The results of this experiment in FIG. 4 showed an increase in binding of THC AIC 10-4 to the THC 2–57-HRP conjugate due solely to an increase in the concentration of $\Delta^9$ THC.

This experiment demonstrates the principle of constructing an immunoassay for a small antigen, specifically a hapten, by utilizing two monoclonal antibodies and the anti-immune complex concept.

Additional experiments indicate that THC AIC 10-4 does not recognize or bind to THC directly or to ordinary protein conjugates of THC as determined by ELISA using THC-horseradish peroxidase as the plate coat. Rather, the monoclonal antibody THC AIC 10-4 specifically shows enhanced binding to a monoclonal antibody, THC 2–57, when such antibody is bound to its antigen, $\Delta^9$ THC. This enhanced specificity of THC AIC 10–4 for THC 2–57 complexed with THC is referred to as anti-immune complex activity.

EXAMPLE 9

Immune Complex ELISA

Fifty μl per well of a 1:400 dilution of affinity-purified rabbit anti-mouse IgG, IgA, IgM antisera (Zymed cat. #61–6400 at 1. mg/ml) was added to 96-well Costar EIA plates, which were then incubated at 37° C. humid incubator.

Before use, the plates were washed three times with ELISA wash buffer (0.01 M $NaH_2PO_4$, 0.15 M NaCl, 0.0290 NaN3, 0.05% Tween, pH 7.2). Fifty μl per well of sample ($Ab_2$) was added and incubated as the previous step. Then 50 μl per well of blocker $IgG_1$ (this was a 1:100 dilution of a 50% saturated $(NH_4)_2SO_4$ precipitation of ascites fluid from an irrelevant $IgG_1$ secreting hybridoma cell line was added to each well and incubated for 15 minutes at room temperature. This irrelevant $IgG_1$ was needed to saturate all non-bound rabbit anti-$IgG_1$ plate coat sites in order to prevent the plate coat from binding to the $IgG_1$ portion of the $Ab_1$-HRP conjugate and giving a false positive signal.

Next, and without washing the plate, 50 μl per well of optimized $Ab_1$-HRP conjugate was added. ($Ab_1$ is a murine monoclonal antibody specific for THC.) One set of replicate plates received just the $Ab_1$-HRP conjugate plus 1:2,000 dilution of 1.0 mg/ml stock THC in ethanol. The plates were again incubated for 15 minutes at room temperature.

The plates were finally washed five times using ELISA wash buffer and 100 μl per well of substrate (0.1 M citrate, pH 4.2, 1.0 mg/ml of ABTS, 1:1,000 dilution of 30% $H_2O_2$) was added to each plate. Once sufficient color had developed, the absorbance at 414 nm was read.

Hybrid cell lines THC 2–57 and THC AIC 10-4 were deposited with the American Type Culture Collection (A.T.T.C.), 12301 Park Lawn Drive, Rockhill, Md. 20852, on Sep. 25, 1986, and received accession numbers HB9214 and HB9213, respectively.

Although the foregoing invention has been described in some detail by way of illustration and example for purposes of clarity of understanding, it will be obvious that certain changes and modifications may be practiced within the scope of the appended claims.

What is claimed is:

1. A monoclonal antibody that exhibits a binding affinity for an immune complex of a monoepitopic antigen and an antibody for said antigen that is substantially greater than the binding affinity for said antigen or said antibody for said antigen apart from said immune complex.

2. The antibody of claim 1 which is AIC 10-4.

3. The antibody of claim 1 wherein said antigen is an organic compound having a molecular weight less than 1500.

4. The antibody of claim 1 wherein said antigen is a drug.

5. The antibody of claim 1 wherein said antigen is tetrahydrocannabinol.

6. The antibody of claim 1 bound to a label.

7. The antibody of claim 6 wherein said label is selected from the group consisting of enzymes, fluorescers, chemiluminescers, co-enzymes, dispersible solid particles, liposomes, radioisotopes, magnetic particles, and solid supports.

8. The antibody of claim 1 which has a binding affinity for said immune complex at least ten times as great as that for said monoepitopic antigen or said antibody for said monoebitobic antigen apart from said immune complex.

9. The monoclonal antibody of claim 1 wherein said antigen is different from the antigen homologous with said antibody for said antigen.

10. A composition comprising an immune sandwich complex of a monoepitopic antigen or analog thereof, a first antibody that binds to said antigen, and a second monoclonal antibody that exhibits a binding affinity for an immune complex of said antigen or said analog and said first antibody that is substantially greater than the binding affinity for said antigen or analog thereof or said first antibody apart from said immune complex.

11. The composition of claim 10 wherein said first antibody is a monoclonal antibody.

12. The composition of claim 10 wherein said monoclonal antibody is AIC 10-4.

13. The composition of claim 10 wherein said antigen is an organic compound having a molecular weight less than 1500.

14. The composition of claim 10 wherein said antigen is a drug.

15. The composition of claim 10 wherein said antigen is tetrahydrocannabinol.

16. A method for determining a monoepitopic antigen of molecular weight less than 1500 in a sample suspected of containing said antigen, which comprises—
   forming an immune sandwich complex comprising said antigen or an analog thereof, a first monoclonal antibody that binds to said antigen, and a second monoclonal antibody that exhibits a binding affinity for an immune complex of said antigen and said antibody for said antigen that is substantially greater than the binding affinity for said hapten or said antibody apart from said immune complex and
   detecting said immune sandwich complex, the amount thereof indicating the amount of said antigen in said sample.

17. The method of claim 16 wherein said immune sandwich complex is bound to a support.

18. The method of claim 16 wherein said first antibody is bound to a support.

19. The method of claim 16 wherein said first antibody is bound to a label.

20. The method of claim 19 wherein said label is selected from the group consisting of enzymes, fluorescers, chemiluminescers, co-enzymes, dispersible solid particles, liposomes, radioisotopes, magnetic particles, and solid supports.

21. The method of claim 16 wherein said sample is combined with said first antibody and said second antibody is subsequently added.

22. The method of claim 16 which is a homogeneous assay method.

23. The method of claim 16 which is a heterogeneous assay method.

24. The method of claim 16 wherein at least one of said antibodies is labeled with a member of the group consisting of enzymes, fluorescers, chemiluminescers, co-enzymes, dispersible solid particles, liposomes, radioisotopes, magnetics particles, and solid supports.

25. The method of claim 16 wherein said monoclonal antibody is AIC 10-4.

26. The method of claim 16 wherein said antigen is a drug.

27. The method of claim 16 wherein said antigen is tetrahydrocannabinol.

28. The method of claim 16 wherein said second antibody has a binding affinity for said immune complex at least ten times as great as that for said antigen or said antibody for said antigen apart from said immune complex.

29. In a homogeneous assay method for the determination of a monoepitopic antigen in a sample suspected of containing said antigen wherein said method comprises the steps of (a) combining in an aqueous medium said sample, labeled antigen, and a first antibody that binds to said antigen and (b) determining the effect of said sample on the amount of first antibody that binds to said labeled antigen as related to the amount of monoepitopic antigen in said sample,
   the improvement which comprises adding to said aqueous medium a second antibody that exhibits a binding affinity for the immune complex of said antigen and said first antibody that is substantially greater than the binding affinity for said antigen or said first antibody apart from said immune complex.

30. The method of claim 29 wherein said label is. an enzyme and the effect of said sample on the enzyme activity of said medium is determined.

31. The method of claim 29 wherein said label is selected from the group consisting of fluorescers, chemiluminescers, co-enzymes, dispersible solid particles, radioisotopes, liposomes, magnetic particles, and solid supports.

32. The method of claim 29 wherein said antibodies are monoclonal antibodies.

33. The method of claim 32 wherein said monoclonal antibody is AIC 10-4.

34. The method of claim 29 wherein said antigen is an organic compound having a molecular weight less than 1500.

35. The method of claim 29 wherein said antigen is a drug.

36. The method of claim 29 wherein said antigen is tetrahydrocannabinol.

37. The method of claim 29 wherein said second antibody has a binding affinity for said immune complex at least ten times as great as that for said antigen or said antibody for said antigen.

38. A kit for use in conducting an assay for a monoepitopic antigen in a sample suspected of containing said antigen, said kit comprising in packaged combination—
   an antibody that exhibits a binding affinity for an immune complex of a monoepitopic antigen and an antibody for said antigen that is substantially greater than the binding affinity for said antigen or said antibody for said antigen apart from said immune complex and reagents for conducting an assay.

39. The kit of claim 38 wherein said antibody is a monoclonal antibody.

40. The kit of claim 39 wherein said monoclonal antibody is AIC 10-4.

41. The kit of claim 39 wherein said antigen is an organic compound having a molecular weight less than 1500.

42. The kit of claim 39 wherein said antigen is a drug.

43. The kit of claim 39 wherein said antigen is tetrahydrocannabinol.

44. A secondary monoclonal antibody against a complex of a molecule of molecular weight less than 1500 and an antibody against said molecule which secondary monoclonal antibody is not an antibody against said molecule or against its antibody.

45. A secondary monoclonal antibody according to claim 44 against a complex of a molecule of molecular weight less than 1500 and a monoclonal antibody against said molecule which secondary monoclonal antibody is not an antibody against said molecule or against its monoclonal antibody.

46. A secondary monoclonal antibody according to claim 45 wherein said molecule is a steroid.

47. A secondary monoclonal antibody according to claim 45 which has a signal generating label.

48. A secondary monoclonal antibody according to claim 47 wherein the signal generating label is a phosphatase.

49. A secondary monoclonal antibody according to claim 45 wherein said molecule is a medicament.

50. A secondary monoclonal antibody according to claim 45 wherein said molecule is estrogen.

51. A secondary monoclonal antibody according to claim 45 wherein said molecule is an aminoglycoside antibiotic.

52. A secondary monoclonal antibody according to claim 45 wherein said molecule is gentamycin.

53. A secondary monoclonal antibody according to claim 45 wherein said medicament is a cardioactive agent.

54. A secondary monoclonal antibody according to claim 45 wherein said molecule is digoxin.

55. A secondary monoclonal antibody according to claim 45 wherein said molecule is a drug of abuse.

56. A secondary monoclonal antibody according to claim 45 wherein the ratio of equilibrium constant between the secondary monoclonal antibody and the complex and the secondary monoclonal antibody and either component of the complex is greater than 10:1.

57. A secondary monoclonal antibody according to claim 45 which is a complete immunoglobulin.

58. A secondary monoclonal antibody according to claim 45 which is an antibody fragment.

59. A secondary monoclonal antibody according to claim 45 which is a Fab or F(ab$^1$)$_2$ fragment.

60. A secondary monoclonal antibody according to claim 44 which has a signal generating label.

61. A secondary monoclonal antibody according to claim 47 wherein the signal generating label is an enzyme.

62. A secondary monoclonal antibody according to claim 61 wherein the enzyme is a phosphatase, peroxidase, galactosidase or dehydrogenase.

63. A secondary monoclonal antibody according to claim 61 wherein the enzyme is an alkaline phosphatase.

64. A secondary monoclonal antibody according to claim 47 wherein the signal generating label is a radiolabel.

65. A secondary monoclonal antibody according to claim 47 wherein the signal generating label is a fluorescent.

66. A secondary monoclonal antibody according to claim 47 wherein the signal generating label is a fluorescein.

67. A secondary monoclonal antibody according to claim 47 labeled with a chemiluminescent moiety.

68. A secondary monoclonal antibody according to claim 61 wherein the label is attached by means of a difunctional reagent.

69. A secondary monoclonal antibody according to claim 47 wherein the molecule is a steroid.

70. A secondary monoclonal antibody according to claim 47 wherein the molecule is a medicament.

71. A secondary monoclonal antibody according to claim 47 wherein said molecule is an aminoglycoside antibiotic.

72. A secondary monoclonal antibody according to claim 47 wherein said molecule is digoxin.

73. A diagnostic kit which contains a secondary monoclonal antibody according to claim 44 and said antibody to the small molecule.

74. A method of determining a molecule of molecular weight less than 1500 which method comprises contacting a suspected source of the molecule with its antibody to form a complex between the molecule and its antibody and with a secondary monoclonal antibody to the complex which secondary monoclonal antibody is not an antibody against said molecule or against its antibody and measuring the association between said complex and said secondary antibody.

75. A method according to claim 74 of determining a molecule of molecular weight less than 1500 which comprises contacting a suspected source of said molecule with a primary monoclonal antibody to said molecule and with a secondary monoclonal antibody to the complex of said molecule and primary monoclonal antibody and measuring the association between said molecule and the primary and secondary monoclonal antibody, which secondary monoclonal antibody is not an antibody against the molecule or against its antibody.

76. A method according to claim 75 wherein the secondary monoclonal antibody has a signal generating label.

77. A method of determining a molecule of molecular weight less than 1500 which comprises contacting a suspected source of said molecule with a primary monoclonal antibody therefor and with a secondary monoclonal antibody to a complex of said molecule and its primary monoclonal antibody which secondary monoclonal antibody is not an antibody against said molecule or its primary monoclonal antibody whereby the secondary monoclonal antibody, molecule and primary monoclonal antibody become associated, and measuring the association between said complex, and the secondary monoclonal antibody.

78. A method according to claim 77 wherein the secondary monoclonal antibody or primary monoclonal antibody has a signal generating label for measuring the association between said complex and the secondary monoclonal antibody.

79. A method according to claim 77 wherein the secondary monoclonal antibody has a signal generating label for measuring the association between said complex and said secondary monoclonal antibody.

80. A method according to claim 77 wherein the primary monoclonal antibody has a signal generating label for measuring the association between said complex and the said secondary monoclonal antibody.

81. A method according to claim 78 wherein the signal generating label is an alkaline phosphatase.

82. A method according to claim 78 wherein the signal generating label is an enzyme.

83. A method according to claim 78 wherein the signal generating label is fluorescent.

84. A method according to claim 78 wherein the signal generating label is chemiluminescent.

85. A method according to claim 82 wherein the signal generating label is an alkaline phosphatase.

86. A method according to claim 77 wherein the primary monoclonal antibody is bound to a surface, a liquid suspected source of said molecule is brought into contact with the surface and the secondary monoclonal antibody which has a signal generating label is also brought into contact with the surface, whereby said molecule and secondary monoclonal antibody become bound to the primary monoclonal antibody, the liquid is separated from the surface and the signal generating label is employed to measure the secondary monoclonal antibody.

87. A method according to claim 86 wherein the signal generating label is an enzyme.

88. A method according to claim 86 wherein the signal generating label is chemiluminescent.

89. A method according to claim 86 wherein the signal generating label is fluorescein.

90. A method according to claim 86 wherein the signal generating label is alkaline phosphatase.

91. A method according to claim 77 for determining a molecule of molecular weight less than 1500 which comprises binding a primary monoclonal antibody to said molecule to a surface, contacting the thus bound primary monoclonal antibody with a liquid suspected source of said molecule and with a secondary monoclonal antibody which has a signal generating label, incubating the system until said molecule and secondary monoclonal antibody become bound to the primary antibody and hence to the surface, separating the liquid from the surface and determining the secondary monoclonal antibody on the surface by employing the signal generating label.

92. A method according to claim 91 wherein the signal generating label is an enzyme.

93. A method according to claim 91 wherein the signal generating label is chemiluminescent.

94. A method according to claim 91 wherein the signal generating label is fluorescent.

95. A method according to claim 91 wherein the signal generating label is alkaline phosphatase.

96. A method, according to claim 77 for determining a molecule of molecular weight less than 1500, which comprises binding said secondary monoclonal antibody to a surface, contacting the thus bound secondary monoclonal antibody with a liquid suspected source of said molecule and with said primary monoclonal antibody, wherein said primary monoclonal antibody has a signal generating label, incubating the system until said molecule and primary monoclonal antibody become bound to said secondary monoclonal antibody and hence to said surface, separating the liquid from the surface and determining the primary monoclonal antibody on said surface by employing the signal generating label.

97. A method according to claim 96 wherein the signal generating label is an enzyme.

98. A method according to claim 96 wherein the signal generating label is alkaline phosphatase.

99. A method according to claim 96 wherein the signal generating label is chemiluminescent.

100. A method according to claim 96 wherein the signal generating label is fluorescent.

101. A method according to claim 77 which is an elisa method.

102. A method according to claim 77 carried out at 5°–45° in an aqueous solution at a pH of 4–11.

103. A polyclonal antibody which comprises a secondary antibody against a complex of a hapten of molecular weight less than 1500 and an antibody against said hapten, said secondary antibody being free from antibodies against the hapten and its antibody.

104. A polyclonal antibody as claimed in claim 103 which comprises a secondary antibody against a complex of a hapten of molecular weight of 100 to 1500 and a primary monoclonal antibody against said hapten, said secondary antibody being free from antibodies against the hapten and its primary monoclonal antibody.

105. A polyclonal antibody according to claim 104 wherein the hapten has a molecular weight of 125 to 1000.

106. A polyclonal antibody according to claim 104 which is labelled whereby it is detectable.

107. A polyclonal antibody according to claim 106 wherein the label is either (a) an enzymatic label or (b) a chemiluminescent or fluorescent label.

108. A polyclonal antibody according to claim 106 wherein the label is alkaline phosphatase.

109. A polyclonal antibody according to claim 103 which is a complete immunoglobulin.

110. A polyclonal antibody according to claim 103 wherein the antibody is a Fab or $F(ab^1)_2$ fragment.

111. A polyclonal antibody according to claim 103 wherein the hapten is a hormone, vitamin, peptide, a therapeutic drug or a drug monitored for police functions.

112. A polyclonal antibody according to claim 103 wherein the hapten is an estrogen, an androgen, an andrecorticol steroid, an antibiotic, morphine, methadone, cannabinol or a cocaine alkaloid.

113. A polyclonal antibody according to claim 104 which comprises a secondary antibody against a complex of an androgen and a primary antibody against said androgen, said secondary antibody being free from antibodies against said androgen and its primary antibody.

114. A polyclonal antibody according to claim 104 wherein the ratio of the equilibrium constants between the secondary polyclonal antibody and the complex and the secondary polyclonal antibody and either component of the complex is greater than 10:1.

115. A polyclonal antibody according to claim 107 wherein the label is a chemiluminescent or fluorescent material.

116. A method of determining a hapten of molecular weight 100 to 1500 which method comprises contacting a suspected source of the hapten with its primary antibody and with a secondary polyclonal antibody to a complex of the hapten and its primary antibody which secondary polyclonal antibody is not an antibody to the hapten or its primary antibody and measuring the association between the complex and the secondary polyclonal antibody and relating said measured association to the amount of said hapten.

117. A method according to claim 116 for the determination of a hapten of molecular weight 125 to 1000 wherein the secondary polyclonal antibody is labeled.

118. A method according to claim 116 which comprises a two site assay in which the primary antibody is bound to a surface.

119. A method according to claim 116 wherein the hapten is a hormone, vitamin, peptide, a therapeutic drug or a drug monitored for police functions.

120. A method according to claim 116 wherein the hapten is an estrogen, an androgen, an andrecorticol steroid, an antibiotic, morphine, methadone, cannabinol or a cocaine alkaloid.

121. A method according to claim 116 wherein the primary antibody is a monoclonal antibody.

* * * * *